(12) United States Patent
Gavalda et al.

(10) Patent No.: US 9,029,576 B2
(45) Date of Patent: May 12, 2015

(54) 5-SEC-BUTYL-2-(2-4-DIMETHYL-CYCLOHEX-3-ENYL)-5-METHYL-[1,3]DIOXANE AND PROCESS FOR MAKING THE SAME

(71) Applicant: International Flavors & Fragrances Inc., New York, NY (US)

(72) Inventors: Juan Adell Gavalda, Benicarlo (ES); Anubhav P. S. Narula, Hazlet, NJ (US); Ana Maria Collado Perez, Benicarlo (ES)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 14/016,880

(22) Filed: Sep. 3, 2013

(65) Prior Publication Data

US 2014/0081034 A1    Mar. 20, 2014

(51) Int. Cl.
*C07D 319/06* (2006.01)
(52) U.S. Cl.
CPC .................................. *C07D 319/06* (2013.01)

(58) Field of Classification Search
CPC ..................................................... C07D 319/06
USPC .......................................................... 549/369
See application file for complete search history.

(56) References Cited

U.S. PATENT DOCUMENTS 2,889,339 A    6/1959  Levy et al.
5,175,143 A *  12/1992 Newman et al. ................ 512/12

FOREIGN PATENT DOCUMENTS

| CN | 101525279 A | 9/2009 |
| EP | 0276998 A2 | 8/1988 |
| JP | S54125613 A | 9/1979 |
| JP | 2009196917 | * 9/2009 |

OTHER PUBLICATIONS

Munro, D., et al., "Lewis acid-catalysed reaction of (cyclo)alkenes with oxiranes." Tetrahedron Letters, 41 (9), Feb. 2000, 1483-1486.
European Search Report, Sep. 10, 2013.

* cited by examiner

*Primary Examiner* — T. Victor Oh
(74) *Attorney, Agent, or Firm* — XuFan Tseng; Zhijun Zhang; Elizabeth M. Quirk

(57) ABSTRACT

The present invention is directed to 5-sec-butyl-2-(2,4-dimethyl-cyclohex-3-enyl)-5-methyl-[1,3]dioxane and a novel process for making the same.

4 Claims, No Drawings

5-SEC-BUTYL-2-(2-4-DIMETHYL-CYCLOHEX-3-ENYL)-5-METHYL-[1,3]DIOXANE AND PROCESS FOR MAKING THE SAME

FIELD OF THE INVENTION

The present invention relates to 5-sec-butyl-2-(2,4-dimethyl-cyclohex-3-enyl)-5-methyl-[1,3]dioxane and a novel process for making the same.

BACKGROUND OF THE INVENTION

There is an ongoing need in the fragrance industry to provide novel processes for making fragrance molecules. It is well recognized by the art that practical considerations such as synthesis may prevent the use of fragrance molecules in commercial applications. Whether the synthesis of a given fragrance molecule can be carried out at a commercial scale is sometimes unpredictable. For this reason, the fragrance industry has made continuous effort to investigate and develop novel and economical processes for making fragrance molecules.

SUMMARY OF THE INVENTION

The present invention is directed to 5-sec-butyl-2-(2,4-dimethyl-cyclohex-3-enyl)-5-methyl-[1,3]dioxane represented by the formula set forth below:

Formula I

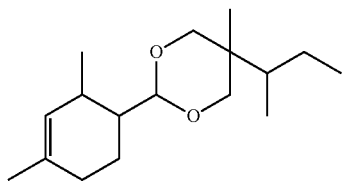

More specifically, the present invention is directed to 2-sec-butyl-2-methyl-propane-1,3-diol, a key intermediate in the synthesis of 5-sec-butyl-2-(2,4-dimethyl-cyclohex-3-enyl)-5-methyl-[1,3]dioxane. 2-sec-Butyl-2-methyl-propane-1,3-diol is represented by the formula set forth below:

Formula II

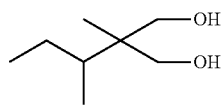

More specifically, the present invention is directed to a novel process of making 2-sec-butyl-2-methyl-propane-1,3-diol.

These and other embodiments of the present invention will be apparent by reading the following specification.

DETAILED DESCRIPTION OF THE INVENTION 5-sec-Butyl-2-(2,4-dimethyl-cyclohex-3-enyl)-5-methyl-[1,3]dioxane has been commercially available as a fragrance material. It possesses woody and ambery notes that are widely applicable in perfumery products. The present invention, however, provides an improved synthetic process of 2-sec-butyl-2-methyl-propane-1,3-diol, which is the key intermediate in the synthesis of 5-sec-butyl-2-(2,4-dimethyl-cyclohex-3-enyl)-5-methyl-[1,3]dioxane. The present process is new, convenient, and economical.

According to the present invention, 2-sec-butyl-2-methyl-propane-1,3-diol can be prepared according to the reaction scheme below, the details of which are specified in the Example. Reagents are all commercially available.

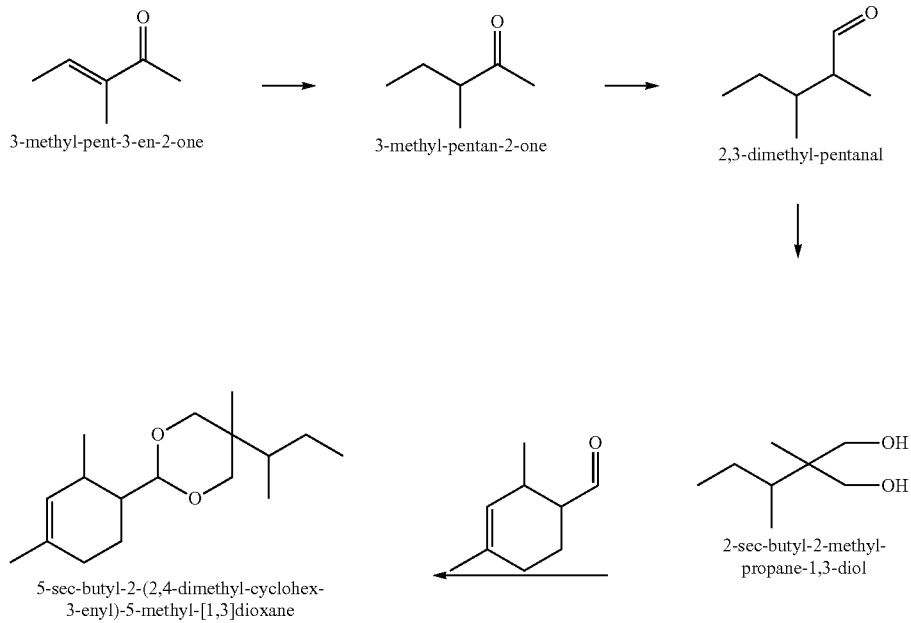

Alternatively, the intermediate 2,3-dimethyl-pentanal in the above reaction scheme can be prepared as follows:

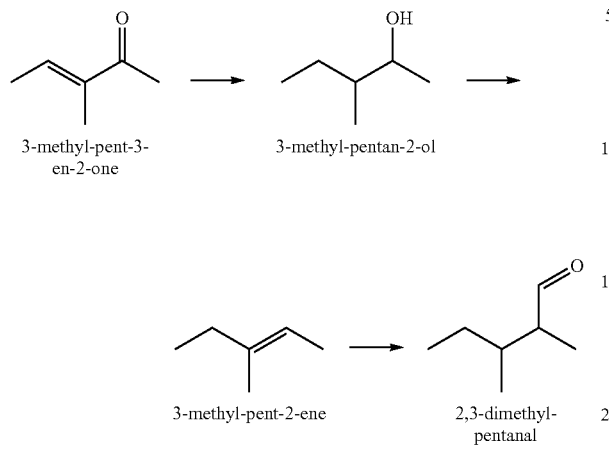

Those with skill in the art will recognize that some of the compounds of the present invention contain a number of chiral centers, thereby providing numerous isomers. It is intended herein that the compounds described herein include the isomeric mixtures, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The following are provided as specific embodiments of the present invention. Other modifications of this invention will be readily apparent to those skilled in the art. Such modifications are understood to be within the scope of this invention. As used herein all percentages are weight percent unless otherwise noted, g is understood to be gram, Kg is understood to be kilogram, and L is understood to be liter. IFF as used in the examples is understood to mean International Flavors & Fragrances Inc., New York, N.Y., USA.

Example I

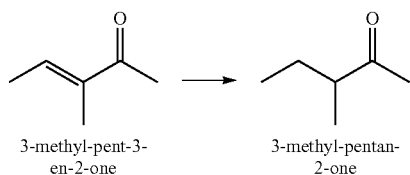

Preparation of 3-Methyl-pentan-2-one

A 2 L pressure vessel was charged with 3-methyl-pent-3-en-2-one (1.23 Kg) and catalyst palladium on carbon (Pd/C) (9.4 g), and reacted with hydrogen at about 85° C. under a pressure of about 10 bar. Gas chromatography (GC) analysis was used to monitor the completion of the reaction. After about 3.5 hours, product 3-methyl-pentan-2-one (1.2 Kg) was obtained.

Example II

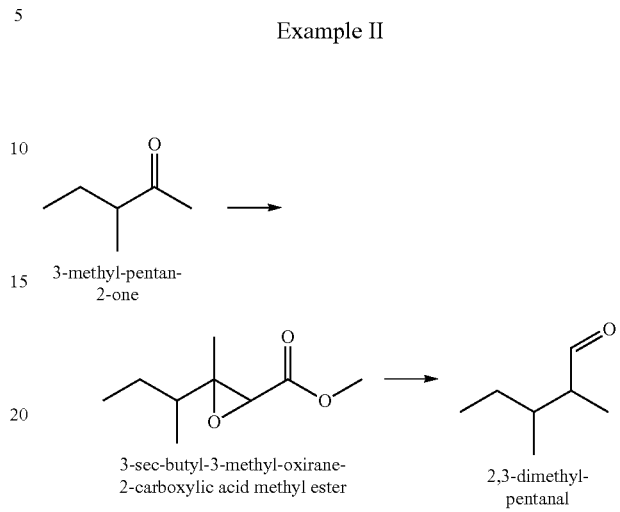

Preparation of 2,3-Dimethyl-pentanal

A reaction flask was charged with a solution of sodium methoxide ($CH_3ONa$) in methanol (2.05 Kg) and heated to 100° C. while methanol (900 g) was recovered via a Bidwell trap. Toluene (1.5 L) was added to the reaction mass and an additional mixture of methanol and toluene (900 g) was recovered. The reaction mass was cooled to 0-5° C. 3-Methyl-pentan-2-one (880 g, prepared as above in EXAMPLE I) was then added in one portion, followed by feeding methyl monochloroacetate ($ClH_2CCOOCH_3$) (1.23 Kg) over a period of 2 hours. The reaction mass was aged for 3 hours while the temperature was allowed to rise to 20° C., and then quenched with aqueous acetic acid ($CH_3COOH$) (2.5%, 2 L). The organic phase was separated and distilled to afford 3-sec-butyl-3-methyl-oxirane-2-carboxylic acid methyl ester (781 g), which was saponified with aqueous sodium hydroxide (NaOH) (20%, 1.2 Kg) to provide 3-sec-butyl-3-methyl-oxirane-2-carboxylate, which was then acidified with phosphoric acid ($H_3PO_4$) to a pH of 2 to provide 3-sec-butyl-3-methyl-oxirane-2-carboxylic acid. The resulting reaction mass containing the carboxylic acid was subsequently decarboxylated by refluxing at 80-90° C. Further distillation afforded product 2,3-dimethyl-pentanal (466 g).

Example III

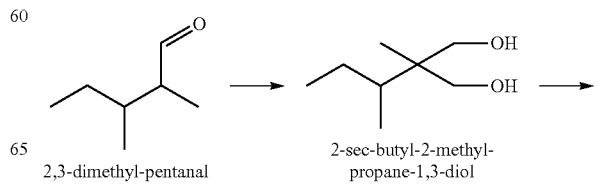

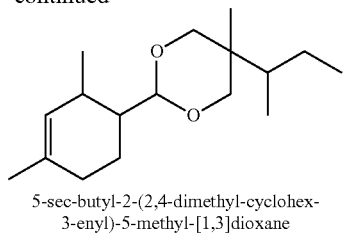

5-sec-butyl-2-(2,4-dimethyl-cyclohex-3-enyl)-5-methyl-[1,3]dioxane

Preparation of 2-sec-Butyl-2-methyl-propane-1,3-diol (Formula II) and 5-sec-Butyl-2-(2,4-dimethyl-cyclohex-3-enyl)-5-methyl-[1,3]dioxane (Formula I)

An aqueous NaOH solution (30%, 420 g) was added at room temperature into a stirred mixture of 2,3-dimethyl pentanal (325 g, prepared as above in EXAMPLE II) and aqueous formaldehyde solution ($CH_2O$) (30%, 722 g) while the reaction temperature was allowed to rise up to about 80° C. due to the exothermic reaction. After the addition was completed, the reaction mixture was cooled to about 40° C. The organic phases was separated and fractionally distilled to afford 2-sec-butyl-2-methyl-propane-1,3-diol (277 g). 2-sec-Butyl-2-methyl-propane-1,3-diol was reacted with 2,4-dimethyl-cyclohex-3-enecarbaldehyde to afford 5-sec-butyl-2-(2,4-dimethyl-cyclohex-3-enyl)-5-methyl-[1,3]dioxane according to previous disclosure (See, for example, U.S. Pat. No. 6,444,637).

Example IV

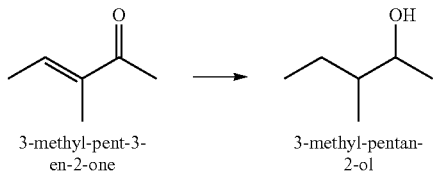

3-methyl-pent-3-en-2-one    3-methyl-pentan-2-ol

Preparation of 3-Methyl-pentan-2-ol

A 2 L pressure vessel was charged with 3-methyl-pent-3-en-2-one (1 Kg) and catalyst Ru/Al (15 g), and reacted with hydrogen at about 150° C. under a pressure of about 30 bar. GC analysis was used to monitor the completion of the reaction. After about 7 hours, product 3-methyl-pentan-2-ol (1.02 Kg) was obtained.

Example V

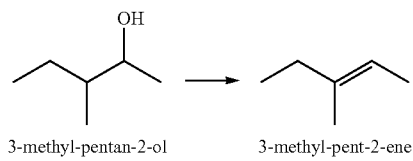

3-methyl-pentan-2-ol    3-methyl-pent-2-ene

Preparation of 3-Methyl-pent-2-ene

3-Methyl-pentan-2-ol (1.218 Kg, prepared as above in EXAMPLE IV) was reacted with methanesulfonic acid ($CH_3SO_3H$) (55 g) at about 130° C. A mixture of the product 3-methyl-pent-2-ene and water was distilled until no more water was formed. Product 3-methyl-pent-2-ene (985 g) was recovered.

Example VI

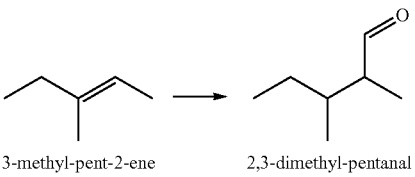

3-methyl-pent-2-ene    2,3-dimethyl-pentanal

Preparation of 2,3-Dimethyl-pentanal

3-Methyl-pent-2-ene (prepared as above in EXAMPLE V) was dried over anhydrous sodium sulfate ($Na_2SO_4$) and then used to prepare 2,3-dimethyl-pentanal according to previous disclosure (See, for example, U.S. Pat. No. 6,444,637).

What is claimed is:
1. A process for preparing 5-sec-butyl-2-(2,4-dimethyl-cyclohex-3-enyl)-5-methyl-[1,3]dioxane consisting essentially of the steps of:
 (i) reacting 3-methyl-pent-3-en-2-one and hydrogen to provide 3-methyl-pentan-2-one;
 (ii) reacting 3-methyl-pentan-2-one of step (i) and methyl monochloroacetate to provide 3-sec-butyl-3-methyl-oxirane-2-carboxylic acid methyl ester;
 (iii) saponifying followed by acidifying and then decarboxylating 3-sec-butyl-3-methyl-oxirane-2-carboxylic acid methyl ester of step (ii) to provide 2,3-dimethyl-pentanal;
 (iv) reacting 2,3-dimethyl-pentanal of step (iii) and sodium hydroxide to provide 2-sec-butyl-2-methyl-propane-1,3-diol; and
 (v) reacting 2-sec-butyl-2-methyl-propane-1,3-diol of step (iv) and 2,4-dimethyl-cyclohex-3-enecarbaldehyde to provide 5-sec-butyl-2-(2,4-dimethyl-cyclohex-3-enyl)-5-methyl-[1,3]dioxane.
2. The process of claim 1, wherein step (i) is carried out at a temperature of about 85° C. and a pressure of about 10 bar.
3. The process of claim 1, wherein step (iii) decarboxylating is by refluxing at about 80-90° C.
4. A process for preparing 5-sec-butyl-2-(2,4-dimethyl-cyclohex-3-enyl)-5-methyl-[1,3]dioxane consisting essentially of the steps of:
 (i) reacting 3-methyl-pent-3-en-2-one and hydrogen at a temperature of about 85° C. and a pressure of about 10 bar to provide 3-methyl-pentan-2-one;
 (ii) reacting 3-methyl-pentan-2-one of step (i) and methyl monochloroacetate to provide 3-sec-butyl-3-methyl-oxirane-2-carboxylic acid methyl ester;
 (iii) saponifying followed by acidifying and then decarboxylating 3-sec-butyl-3-methyl-oxirane-2-carboxylic acid methyl ester of step (ii) to provide 2,3-dimethyl-pentanal, wherein decarboxylating is by refluxing at about 80-90° C.;

(iv) reacting 2,3-dimethyl-pentanal of step (iii) and sodium hydroxide to provide 2-sec-butyl-2-methyl-propane-1,3-diol; and (v) reacting 2-sec-butyl-2-methyl-propane-1,3-diol of step (iv) and 2,4-dimethyl-cyclohex-3-enecarbaldehyde to provide 5-sec-butyl-2-(2,4-dimethyl-cyclohex-3-enyl)-5-methyl-[1,3]dioxane.

* * * * *